US010639171B2

(12) United States Patent
Cavuto et al.

(10) Patent No.: US 10,639,171 B2
(45) Date of Patent: May 5, 2020

(54) TRANSFEMORAL ROTATOR USING PUSH BUTTON SPRING CLIPS

(71) Applicant: Massachusetts Institute of Technology, Cambridge, MA (US)

(72) Inventors: Matthew L. Cavuto, Cambridge, MA (US); Matthew L. Chun, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 146 days.

(21) Appl. No.: 15/398,159

(22) Filed: Jan. 4, 2017

(65) Prior Publication Data

US 2017/0216054 A1   Aug. 3, 2017

Related U.S. Application Data

(60) Provisional application No. 62/287,969, filed on Jan. 28, 2016.

(51) Int. Cl.
*A61F 2/76* (2006.01)
*A61F 2/50* (2006.01)
*A61F 2/60* (2006.01)
*A61F 2/68* (2006.01)

(52) U.S. Cl.
CPC ........ *A61F 2/76* (2013.01); *A61F 2002/5018* (2013.01); *A61F 2002/5072* (2013.01); *A61F 2002/607* (2013.01); *A61F 2002/6854* (2013.01)

(58) Field of Classification Search
CPC ...... A61F 2/60; A61F 2/76; A61F 2002/5016; A61F 2002/5018; A61F 2002/5039; A61F 2002/5043; A61F 2002/5081; A61F 3/00; Y10T 403/606
See application file for complete search history.

(56) References Cited

U.S. PATENT DOCUMENTS

| 4,306,320 A | * | 12/1981 | Delp | ......................... A61F 2/66 |
| | | | | 623/48 |
| 4,616,668 A | * | 10/1986 | Battiston | .................. A45B 9/00 |
| | | | | 135/75 |
| 7,785,373 B2 | * | 8/2010 | Frye, Jr. | .................... A61F 2/60 |
| | | | | 623/45 |

(Continued)

FOREIGN PATENT DOCUMENTS

| WO | 2011/117387 A1 | 9/2011 |
| WO | 2017/132193 A1 | 8/2017 |

OTHER PUBLICATIONS

International Search Report for PCT/US2017/014823 dated Apr. 12, 2017.

(Continued)

*Primary Examiner* — Christie L Bahena
(74) *Attorney, Agent, or Firm* — Hamilton, Brook, Smith & Reynolds, P.C.

(57) ABSTRACT

A transfemoral rotator is provided. The transfemoral rotator includes an inner cylinder that nests within a cavity of a base shell. The inner cylinder includes a lower cylindrical hub configured to protrude through an opening in the base shell. A spring clip mechanism operated by a push button serves to lock and unlock the transfemoral rotator to permit for rotation of a lower limb prosthesis and allow for a wearer to sit cross-legged.

10 Claims, 4 Drawing Sheets

(56) References Cited

U.S. PATENT DOCUMENTS

2012/0065742 A1* 3/2012 Wu .................. A61F 2/644
 623/39
2014/0222166 A1 8/2014 Olafsson et al.
2014/0358248 A1 12/2014 Will

OTHER PUBLICATIONS

International Preliminary Report on Patentability dated Aug. 9, 2018 for International Application No. PCT/US2017/014823, entitled "Transfemoral Rotator Using Pushbutton Spring Clips.".

* cited by examiner

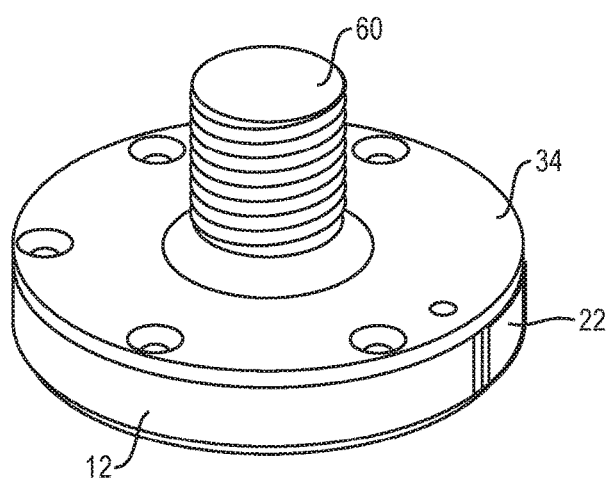
FIG. 6
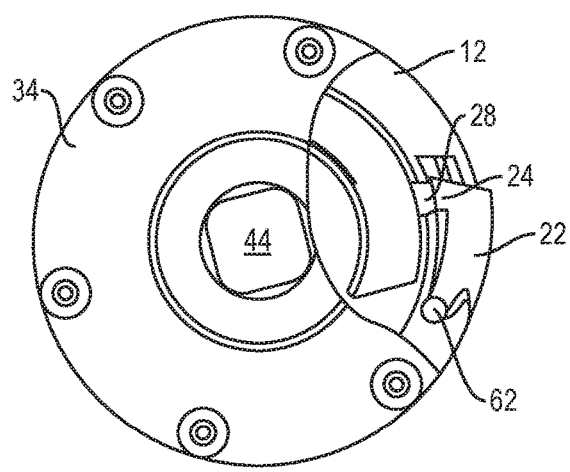 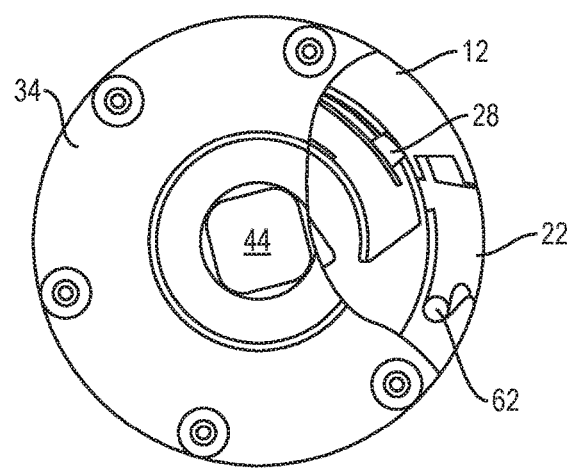
FIG. 7  FIG. 8

TRANSFEMORAL ROTATOR USING PUSH BUTTON SPRING CLIPS

This application claims priority to US Provisional Patent Application Ser. No. 62/287,969 filed on Jan. 28, 2016, the contents of which are incorporated herein by reference.

BACKGROUND OF THE INVENTION

Transfemoral rotators are devices that allow above-knee amputees to sit cross-legged while wearing a prosthesis. The transfemoral rotator fits between an amputee's socket and a prosthetic knee, and allows for rotation of distal prosthetic components along a longitudinal axis. Present day transfemoral rotators in developed nations are typically made of expensive materials and can cost thousands of dollars. These devices are also extremely complex and typically include 20-50 components.

The transfemoral rotator disclosed herein allows for a much simpler and lower cost design. The disclosed design has applications for the developing world by allowing for a low cost and simple structure to achieve previously unattainable rotation of a lower limb prosthesis thereby increasing quality of life for above-knee amputees.

SUMMARY OF THE INVENTION

The transfemoral rotator according to the invention includes a base shell having a cylindrical central cavity therein and having a lower opening and further including a button-retaining recess for holding a button for movement in a peripheral location of the base shell. An inner cylinder is nested for rotation within the base shell central cavity. The inner cylinder includes a lower cylindrical hub sized to protrude through the lower opening in the base shell, the inner cylinder further including a spring clip-retaining recess for receiving a U-shaped, pushbutton, spring clip. The U-shaped spring clip has a dimple protruding through a hole in the inner cylinder and through a hole in the base shell to lock the inner cylinder with respect to the base shell. The pressing of the button will unlock the inner cylinder with respect to the base shell allowing the inner cylinder to rotate freely through 360 degrees. The base shell is also adapted to receive a top plate having a connector and wherein the lower cylindrical hub includes a connector that may be a set screw connector.

In a preferred embodiment, the button includes a dimple for engaging the dimple in the U-shaped spring clip. It is preferred that the top plate include a domed portion and wherein the connector is a tapered square connector or a threaded screw connector.

BRIEF DESCRIPTION OF THE DRAWING

FIG. 6 is a perspective view of an alternative connector embodiment on the top plate.

FIG. 7 is a plan view of an alternative embodiment of the invention in which the push button is hinged.

FIG. 8 is a plan view of the embodiment in FIG. 7 that has been unlocked for rotation.

DESCRIPTION OF THE PREFERRED EMBODIMENT

Figure 1:
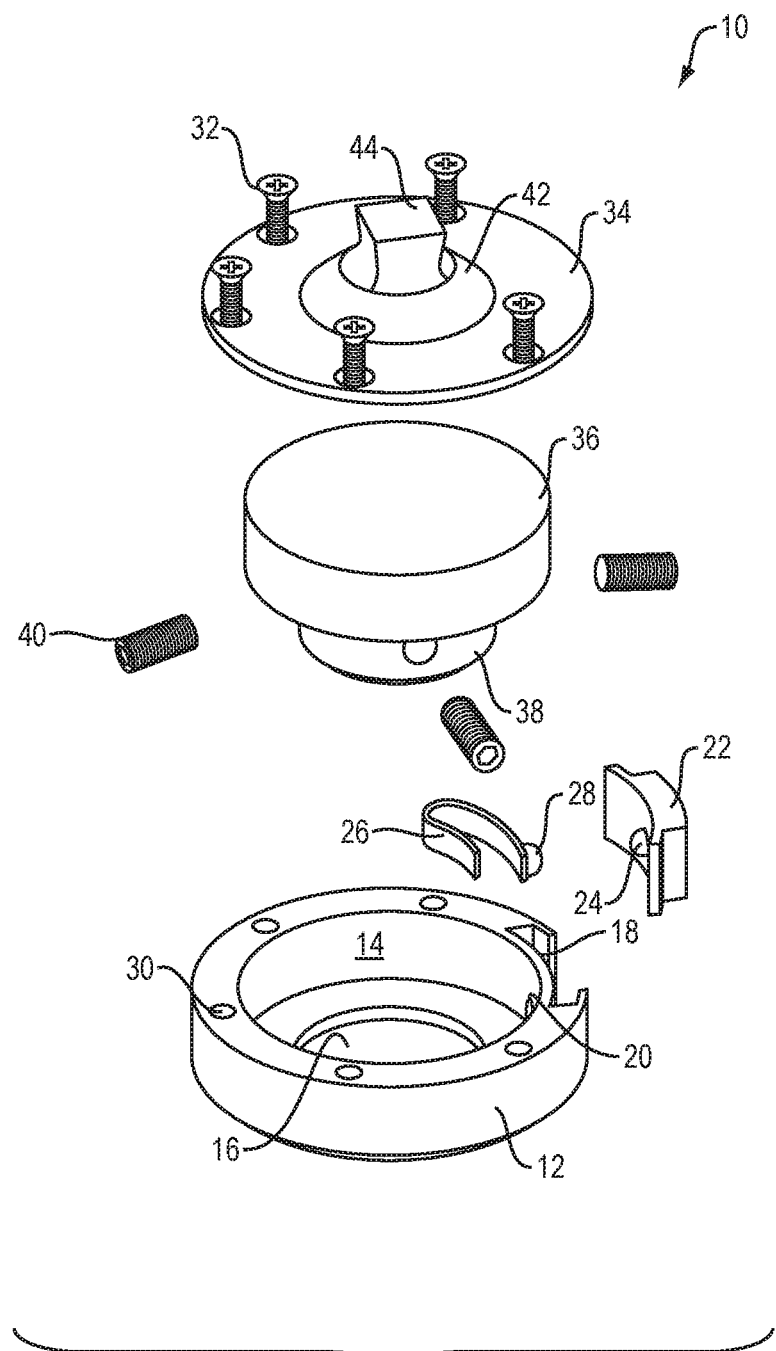
FIG. 1 is an exploded, perspective view of an embodiment of the invention showing all of the parts.

With respect to FIG. 1, a transfemoral rotator 10 includes a base shell 12 having a central cavity 14 therein and includes a relief hole 16 in its lower portion. The base shell 12 includes an inner wall 18 forming a button cavity 20. A push button 22 is configured to fit within the button cavity 20. The button 22 includes a protruding button dimple 24.

A pushbutton spring clip 26 is U-shaped and includes a dimple 28 (e.g., a protrusion). Threaded holes 30 receive bolts 32 for securing a top plate 34 to the base shell 12.

An inner cylinder 36 is adapted to nest in the cavity 14 of the base shell 12. A lower cylindrical hub 38 will protrude through the hole 16. Set screws 40 are used to attach the lower cylindrical hub 38 to an external connector. It is also preferred that the top plate 34 include a domed portion 42 along with a tapered square connector 44.

Figure 2:
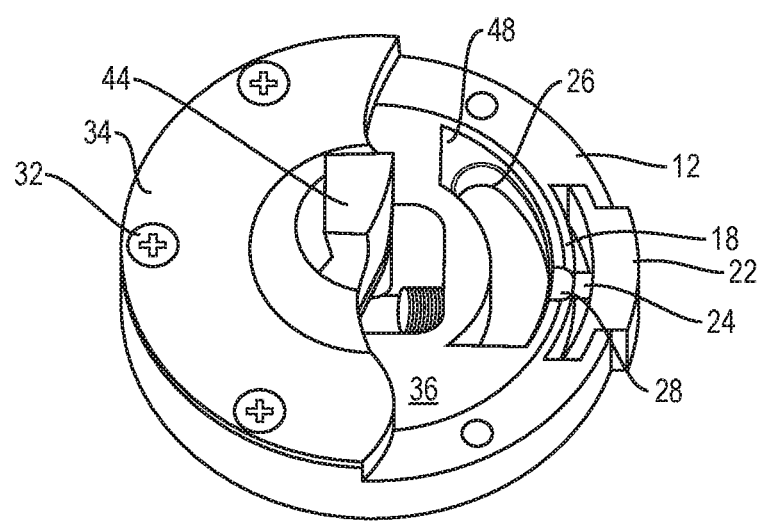
FIG. 2 is a perspective, cutaway view of an embodiment of the invention showing the internal mechanism in a locked state.
Figure 3:
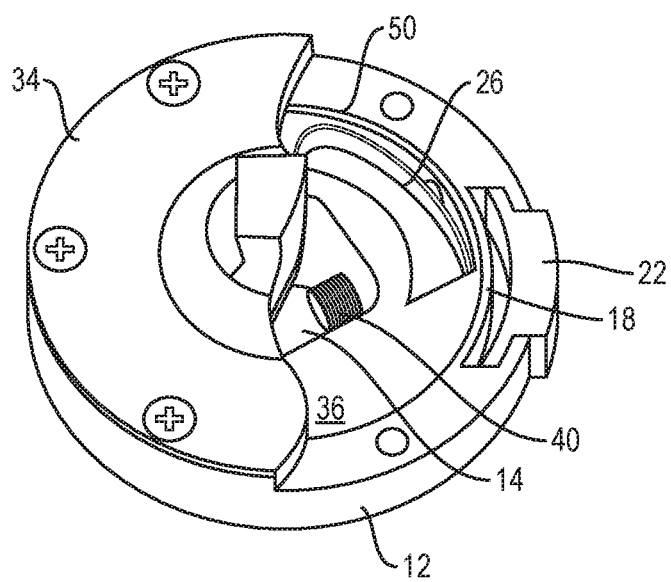
FIG. 3 is a perspective, cutaway view of an embodiment of the invention showing the internal mechanism in an unlocked state.

With reference now to FIGS. 2 and 3 in conjunction with FIG. 1, the spring clip 26 fits in a cavity 48. The spring clip 46 urges the dimple 28 through a hole in the inner wall 18 to engage the dimple 24 on the button 22.

As shown in FIG. 2, the inner cylinder 36 is locked with respect to the base shell 12.

As shown in FIG. 3, upon pushing on the button 22 the dimple 28 is pushed out of the hole thereby unlocking the inner cylinder 36 with respect to the base shell 12 allowing the inner cylinder to rotate freely with respect to the base shell 12. Also shown is the inner cylinder outer wall 50.

Figure 4:
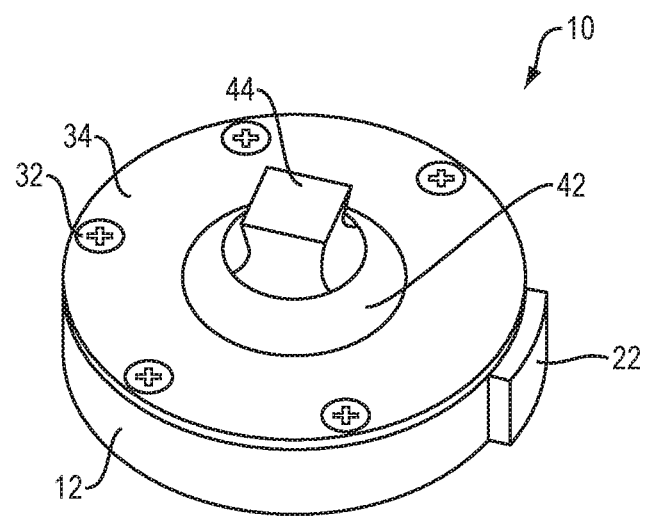
FIG. 4 is a perspective top view of an embodiment of the invention.
Figure 5:
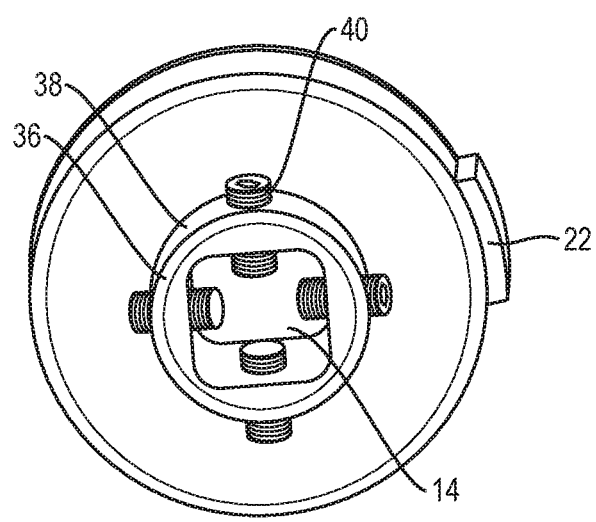
FIG. 5 is a perspective bottom view of an embodiment of the invention.

The assembled transfemoral rotator 10 disclosed herein is shown in FIGS. 4 and 5. Those of ordinary skill in the art will understand that the tapered square connector 44 can be used to attach to an amputee's socket or to a prosthetic device. Similarly, lower cylindrical hub 38 includes the set screws 40 for attachment to a prosthesis or to the socket of an amputee.

With reference again to FIGS. 2 and 3, those of skill in the art will recognize that when an amputee wishes to cross a prosthesis, the button 22 is pushed to release the inner cylinder with respect to the base shell permitting up to 360 degrees of rotation, allowing the crossing of one's legs.

With reference now to FIG. 6, an alternative embodiment includes a threaded screw connector 60 extending from the top plate 34. The threaded screw connector 60 is adapted to attach to a prosthesis as will be appreciated by those of skill in the art.

With reference now to FIGS. 7 and 8, the push button 22 is hinged at 62 at one end. In FIG. 7, the femoral rotator is in the locked position. Upon depressing the push button 22, it will pivot about the pivot point 62 depressing the button 28 thereby releasing the femoral rotator into its unlocked position as shown in FIG. 8.

It is recognized that modifications and variations of the present invention will be apparent to those of ordinary skill in the art and it is intended that all such modifications and be included within the scope of the appended claims.

What is claimed is:

1. Transfemoral rotator configured to couple an upper, proximal prosthetic device to a lower, distal prosthetic device, the upper, proximal prosthetic device configured to couple to a user's limb, the transfemoral rotator comprising:
- a base shell including a cylindrical central cavity therein, a bottom surface, and a button-retaining recess for holding a button for movement in a peripheral location of the base shell, the bottom surface including an opening having a diameter smaller than a diameter of the cylindrical central cavity;
- an inner cylinder nested for rotation within the base shell central cavity, the inner cylinder including a lower cylindrical hub sized to protrude through the opening in the base shell and a top portion having a diameter greater than the diameter of the opening of the base shell, the inner cylinder further including a spring clip-retraining recess for receiving a U-shaped spring clip; the U-shaped spring clip having a protrusion configured to protrude through a hole in the inner cylinder and through a hole in the base shell to lock the inner cylinder with respect to the base shell;
- wherein depressing the button will unlock the inner cylinder with respect to the base shell allowing the inner cylinder to rotate freely; and
- wherein the base shell receives a top plate having a first connector configured to attach to the upper, proximal prosthetic device, the lower cylindrical hub includes a second connector configured to attach to the lower, distal prosthetic device, and the top portion of the inner cylinder is enclosed within the cylindrical central cavity by the base shell and the top plate and axially supported by the base shell.

2. The transfemoral rotator of claim 1 wherein the button includes a protrusion for engaging the protrusion of the U-shaped spring clip.

3. The transfemoral rotator of claim 1 wherein the top plate includes a domed portion.

4. The transfemoral rotator of claim 1 wherein the first connector is a tapered square connector.

5. The transfemoral rotator of claim 1 wherein the first connector is a threaded screw connector.

6. The transfemoral rotator of claim 1 wherein the second connector is a set screw connector.

7. The transfemoral rotator of claim 1 wherein the second connector is a threaded screw connector.

8. The transfemoral rotator of claim 1 wherein the lower cylindrical hub and top portion of the inner cylinder are unitary.

9. The transfemoral rotator of claim 1 wherein the lower, distal prosthetic device is a prosthetic knee.

10. The transfemoral rotator of claim 1 wherein the upper, proximal prosthetic device is a socket of an amputee.

* * * * *